United States Patent [19]

Braestrup et al.

[11] 4,280,993

[45] Jul. 28, 1981

[54] PROCESS FOR DETERMINING THE CONCENTRATION OF BENZODIAZEPINES IN A BODY FLUID

[76] Inventors: Claus Braestrup, Ibstrupvej 48, DK-2820 Gentofte, Denmark; Richard F. Squires, CNS Biology Medical Research Laboratories, Lederle Laboratories, Pearl River, N.Y. 10965

[21] Appl. No.: 4,619

[22] Filed: Jan. 18, 1979

[30] Foreign Application Priority Data

Jan. 19, 1978 [GB] United Kingdom ................ 2164/78

[51] Int. Cl.³ .................... G01N 33/48; A61K 43/00; G01T 1/00
[52] U.S. Cl. ......................................... 424/1; 422/61; 23/230 B; 424/1.5; 424/12
[58] Field of Search ............................ 424/1, 12, 11.5; 23/230 B; 422/61

[56] References Cited

U.S. PATENT DOCUMENTS

| | | | |
|---|---|---|---|
| 3,335,295 | 8/1967 | Sternbach et al. | 260/239.3 D |
| 3,336,296 | 8/1967 | Bell et al. | 260/239.3 D |
| 3,338,886 | 8/1967 | Berger et al. | 260/239.3 D |
| 3,546,212 | 12/1970 | Feux et al. | 260/239.3 D |
| 4,022,878 | 5/1977 | Gross | 424/1.5 |
| 4,083,948 | 4/1978 | Davis et al. | 23/230 B |

OTHER PUBLICATIONS

Peskov et al., J. Pharmactl. Exp. Ther., vol. 186, No. 1, Jul. 1973, pp. 167–172.

Primary Examiner—Benjamin R. Padgett
Assistant Examiner—Christine M. Nucker
Attorney, Agent, or Firm—William J. Daniel

[57] ABSTRACT

A process for determining the concentration of benzodiazepines in a body liquid comprising the steps of contacting freeze-dried brain tissue with tritium labelled flunitrazepam to bond labelled flunitrazepam to receptor sites of the brain tissue, determining the concentration of labelled flunitrazepam of the brain tissue, incubating the brain tissue containing labelled flunitrazepam with a sample of body liquid containing benzodiazepine, the concentration of which is to be determined, to induce displacement of labelled flunitrazepam from said brain tissue, determining the concentration of labelled flunitrazepam bonded to the brain tissue after establishing equilibrium conditions and determining the concentration of benzodiazepine in the body liquid based on the change of concentration of labelled flunitrazepam induced by benzodiazepine contained in the sample.

13 Claims, 1 Drawing Figure

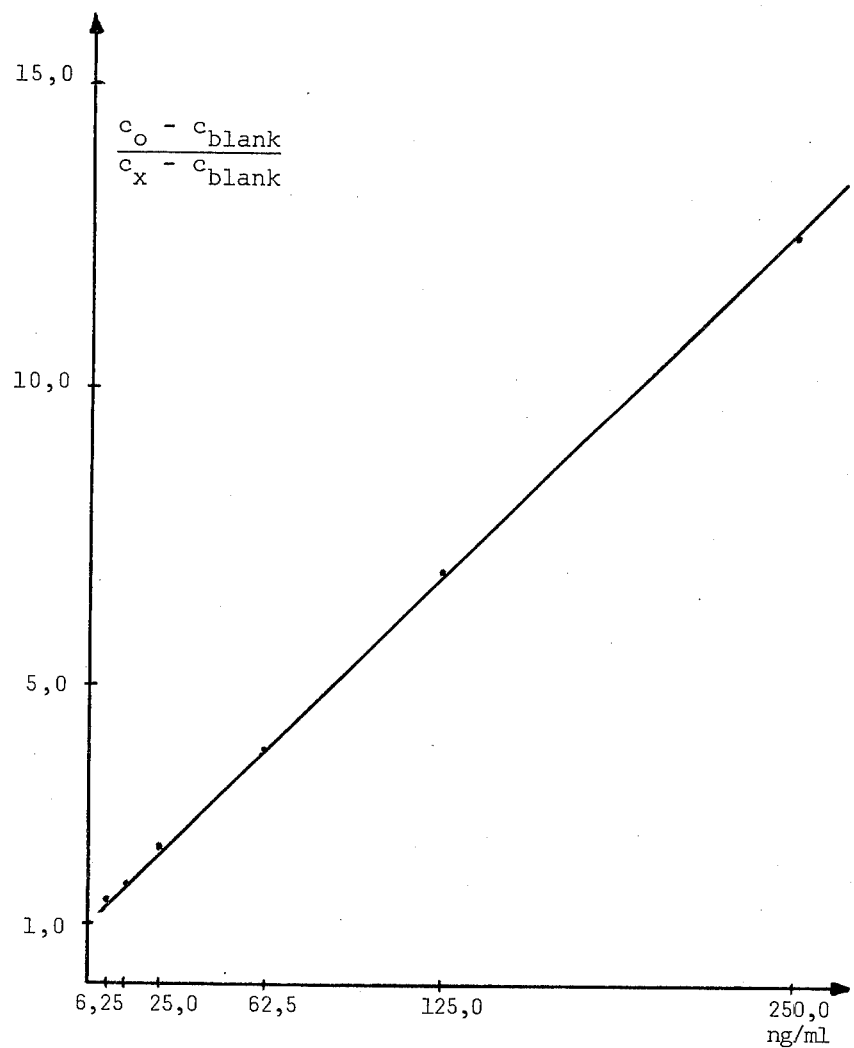

PROCESS FOR DETERMINING THE CONCENTRATION OF BENZODIAZEPINES IN A BODY FLUID

BACKGROUND OF THE INVENTION

It has been reported that radio-labelled butyrophenones, $^3$H-haloperidol and $^3$H-spiroperidol bind selectively and with high affinity to dopamine receptor sites in mamalian brain and that this specific binding is reduced by neuroleptics in concentrations substantially lower than those occurring in the blood of patients at therapeutic doses.

Creese, J., and Snyder, S. H., Nature, 270, 180–182 (1977) describes an assay for neuroleptics based on competition for such dopamine binding.

It has also reported that benzodiazepines bind to specific receptors on the membranes of rats and human brains and that diazepam specifically binds to brain membranes with high affinity (Squires, R. F., and Braestrup, C., Nature 266, 732–734, (1977) and Braestrup, C., and Squires, R. F., Proc.Natl.Acad.Sci.USA, 74, No. 9, 3805–3809 (1977)). It also appears from these articles that $^3$H-diazepam specifically binds to brain membranes with high affinity and that clinically active benzodiazepines have varying ability to displace $^3$H-diazepam from the receptors.

Benzodiazepines represent a major group of drugs and for several reasons it would be desirable to determine by a simple, sensitive and specific test procedure the concentration of a psychotropically active benzodiazepine in patient blood or other body liquid after administration of said drug.

The available assays for individual benzodiazepines including gas chromatography, fluorimetry, etc. have not attained routine clinical use because of technical complexities or restrictions of specificity to benzodiazepines.

The object of the invention is to provide a simple, sensitive and specific assay for benzodiazepines in a body liquid, utilizing stable reagents.

Another object of the invention is to provide an assay for benzodiazepines in a body liquid which assay is suitable for routine clinical application.

A further object of the invention is to provide a receptor reagent for use in the process of the invention.

A still further object of the invention is to provide a kit for use in carrying out the process of the invention.

SUMMARY OF THE INVENTION

These and other objects which will appear from the following disclosure are achieved by the process of the invention which comprises contacting freeze-dried brain tissue with a radio-labelled benzodiazepine to form a preparation comprising said brain tissue and labelled benzodiazepine reversibly bonded thereto, determining the concentration of radio-labelled bound benzodiazepine in said preparation, contacting a sample of the body liquid or an extract of such liquid containing the benzodiazepine, the concentration of which is to be determined, with said preparation to establish an equilibrium between labelled and un-labelled benzodiazepines bonded to said brain tissue, determining the concentration of labelled benzodiazepine bonded to said brain tissue after establishing equilibrium conditions and calculating the concentration of benzodiazepine in the sample based on the change of concentration of labelled benzodiazepine in the brain tissue induced by benzodiazepines contained in the sample.

Freeze-dried brain tissue presents the advantage that it can be stored in the form of a dry powder over long periods without losing its binding activity. Thus, the binding activity of freeze-dried brain tissue as far as tritium labelled flunitrazepam and diazepam is concerned, has been found to be stable at room temperature for at least one year. If stored at lower temperatures, the freeze-dried product can be maintained stable for much longer periods. Thus, the half-lives of the binding activity can be extended up to years. The freeze-dried brain tissue is preferably prepared from ox, pig or sheep brains or from hen or duck brains. However, it may be prepared from the brains of any tetrapods or higher bony fish.

It has been found that the specific $^3$H-diazepam binding in rat brains show an uneven regional distribution. The greatest binding has been found in the frontal and occipital cortex wherein the binding is four times higher than the lowest binding in the pons-medulla. The hippocampus exhibit intermediate binding capacity.

The freeze-dried brain tissue is preferably prepared by homogenizing brain tissue in an aqueous solution of an inert water soluble substance and by freeze-drying the homogenate thus obtained in a manner which is well known per se.

By using an aqueous solution containing a dissolved inert substance, e.g. a sugar, such as sucrose, a porous and friable freeze-dried product which easily can be pulverized is obtained.

Such a powdered product is easily manipulated and can quickly be suspended in an aqueous medium to form a homogeneous suspension.

The freeze-dried brain tissue, preferably in the form of a suspension in an aqueous medium, is then contacted with a radio-labelled benzodiazepine.

Preferred benzodiazepines are flunitrazepam, lorazepam and diazepam. Flunitrazepam is particularly advantageous because in that case the labelled benzodiazepine can be used at room temperature.

It is preferable to label the benzodiazepine with tritium but also other radioactive elements, such as iodine, may be used.

A buffered suspension of powdered brain tissue is preferably contacted with a solution, e.g. an ethanolic or aqueous solution, of the radio-labelled benzodiazepine to form a preparation in which the concentration of labelled benzodiazepine preferably is 1–5 nanomolar.

The exact concentration of the labelled benzodiazepine bonded to said brain tissue can be determined by scintillation counting.

The preparation thus obtained is contacted with a sample or an extract of the body fluid containing the benzodiazepines, the concentration of which is to be determined, and the mixture is preferably incubated at room temperature for a period of from 10 to 120 min. Ordinarily, equilibrium conditions have been established after 20 min. at room temperature. Thus, the benzodiazepines present in the sample have displaced some of the radio-labelled benzodiazepine from the receptor sites of the brain tissue by a competitive displacement.

After incubating the mixture of the preparation and the sample, the brain tissue is isolated preferably by filtration and the concentration of labelled benzodiazepine is determined, preferably by scintillation counting.

The change of concentration of radio-labelled diazepine bonded to the brain tissue is proportional to the concentration of the concentration of benzodiazepines in the sample of the body liquid. Therefore, the latter concentration can be calculated by comparing the change referred to above with a standard curve showing the displacing effect of known quantities of unlabelled benzodiazepines.

In case of determining the concentration of benzodiazepines in whole blood samples, it is desirable to add 1-tryptophan to the suspension of brain tissue because 1-tryptophan competes with benzodiazepines in binding to serum albumin but not to the brain tissue receptors.

It should be mentioned that the process of the invention is suitable for determining the concentration of benzodiazepines in other body liquids than whole blood. Thus, it can be used for assaying e.g. urine, plasma and saliva.

A kit for carrying out the process described above comprises
(a) a container containing freeze-dried brain powder,
(b) a vial containing a solution of radioactively labelled benzodiazepine,
(c) a container containing a buffer solution and
(d) a container containing a solution of a predetermined amount of unlabelled benzodiazepine.

The benzodiazepine contained in the solution containing a predetermined amount of unlabelled benzodiazepine is preferably flunitrazepam, diazepam or lorazepam (7-chloro-5-(2-chlorophenyl)-3-hydroxy-2,3-dihydro-1H-1,4-benzodiazepin-2-one).

The invention will now be described in further detail with reference to the following examples:

EXAMPLE 1

The reagents used were the following:
(a) A 25 mM solution of a sodium phosphate buffer, pH 7.0 (Solution I).
(b) A solution containing 18 ng and 5 μCi of $^3$H-flunitrazepam in 10 ml of 10% ethanol in Solution I (Solution II).
(c) About 0.3 g of a receptor powder, prepared as described below, suspended in 30 ml of Solution I (Suspension III).
(d) A standard solution (IV) containing 20 ng/ml of lorazepam, and prepared by dilution with the buffer I of 0.5 ml of 93% ethanolic solution (IVa) of lorazepam, containing 1 μg/ml of lorazepam, to a volume of 25 ml.

The assaying is performed as follows:

To 15 ml test tubes, each containing 400 μl of the receptor suspension III, are added 100 μl of Solution II and 50 μl of the sample, or 50 μl of the standard solution IV. The tubes are incubated at room temperature for at least 20 minutes and maximum 2 hours. Then, 10 ml of isothermic I are added, and the mixture is immediately filtered through a Whatman GF/C glassfibre filter and washed with 10 ml of isothermic buffer solution I.

The washed filter is placed in a scintillation vial, containing 5 ml of conventional scintillation fluid, and counted shortly after for 0.5 minute, or better the next day for 5 minutes.

For the preparation of a standard curve, a series of dilutions of the lorazepam standard solution (IV) is prepared by diluting with the buffer I, and assaying is performed in duplicate with 50 μl of each of these dilutions being added to the test tubes, each of which contains 400 μl of the suspension III and 100 μl of the solution II.

The results are tabulated below.

TABLE

| Tube No. | Kind | Addition 50 μl of | Counts per minute | $\frac{c_o - c_{blank}}{c_x - c_{blank}}$ |
|---|---|---|---|---|
| 1-2 | control | I | 2790 | — |
| 3-4 | blank | IVa | 156 | — |
| 5-6 | sample | drug 250 ng/ml | 402 | 12.51 |
| 7-8 | sample | drug 125 ng/ml | 601 | 6.87 |
| 9-10 | sample | drug 62.5 ng/ml | 944 | 3.86 |
| 11-12 | control | I | 3104 | — |
| 13-14 | control | I | 3500 | — |
| 15-16 | blank | IVa | 164 | — |
| 17-18 | sample | drug 25 ng/ml | 1477 | 2.30 |
| 19-20 | sample | drug 12.5 ng/ml | 1910 | 1.73 |
| 21-22 | sample | drug 6.25 ng/ml | 2313 | 1.41 |
| 23-24 | control | I | 3353 | — |

The figures in the column to the right are arrived at as follows:

The average of counts $c_o$ from the controls is 3187 from which is subtracted the average of the counts from the blanks, which is 160, to give $c_o - c_{blank}$.

The count $c_x$ from each sample also has to be reduced by the average counts from the blanks, resulting from background radiation, to give $c_x - c_{blank}$.

In the accompanying drawing, the test results are plotted as $c_o - c_{blank}/c_x - c_{blank}$ versus the concentration of lorazepam, and the standard curve, therefore, can be used for quantitative determination of the benzodiazepine contents of samples.

The receptor powder used in the process described above was ox brain tissue which had been homogenized in 3 volumes of iced 1M sucrose solution whereafter the homogenate had been freeze-dried.

EXAMPLE 2

This example illustrates the preparation of three other types of receptor powder suitable for use in the process described in Example 1.

(a) 10 g pig whole forebrain is homogenized in 30 ml of iced 1 M sucrose solution and the homogenate thus obtained is freeze-dried. The freeze-dried product is pulverized and used as the animal brain tissue powder in the process described in Example 1. Control assays, cf. tubes 1 and 2 of the table of Example 1, will give 3110 cpm, and blank assays, cf. tubes 3 and 4 of the table of Example 1, will give 260 cpm.

(b) 10 g whole rat forebrain is homogenized in 30 ml of iced 1 M sucrose solution and the homogenate is freeze-dried. The freeze-dried product is pulverized and used as the animal brain tissue powder in the process described in Example 1. Control assays, cf. tubes 1 and 2 of the table of Example 1, will give 3625 cpm. Blank assays, cf. tubes 3 and 4 of the table of Example 1, will give 191 cpm.

(c) 10 g hen whole forebrain is homogenized in 30 ml of ized 1 M sucrose solution and the homogenate is freeze-dried. The freeze-dried product is pulverized and used as the brain tissue powder in the process described in Example 1. Control assays, cf. tubes 1 and 2 of the table of Example 1, will give 1831 cpm. Blank assays, cf. tubes 3 and 4 of the table of Example 1, will give 126 cpm.

EXAMPLE 3

The following procedure was used:

A 0.5 ml sample of body fluid is extracted with 1.00 ml ethyl acetate. 0.5 ml of the organic extract is evaporated in vacuo. The residue is dissolved in 50 μl sodium phosphate (25 mM, pH 7.5) and added 400 μl receptor suspension and 100 μl tritium labelled flunitrazepam solution (1.8 ng and 0.5 μCi per ml), final concentration 1 nM. After 10-120 min. at room temperature 10 ml sodium phosphate is added and the mixture is filtered immediately through a glassfibre filter (Millipore GF/C) using a Millipore filtering device. The filter is washed with 10 ml sodium phosphate. The radioactivity of the filter is determined by liquid scintillation (Packard 3320: Gain 50%, Window 50-330) using 10 ml Dimilume ® as scintillation liquid.

The following reference samples were processed as described above:

(a) Two samples of sodium phosphate (each 50 μl),
(b) two samples of a lorazepam solution containing 1 μg/ml (each 50 μl),
(c) 8 standard solutions of lorazepam containing 5-50 ng/ml (each 50 μl).

These solutions were not extracted with ethyl acetate but were treated simultaneously with the residues dissolved in 50 μl sodium phosphate. They were used for calculation of the concentration of lorazepam in the sample.

According to the procedure described samples of human blood, plasma, urine and saliva with added known amounts of lorazepam have been analysed. The results are given in Table 1.

If the samples to be analysed contain high concentrations of benzodiazepine, then the extraction with ethyl acetate can be omitted and 50 μl samples or less analysed directly. Results obtained by using this modified procedure are given in Table 2.

The sensivity is >1 ng/ml lorazepam with the extraction method, and about 20 ng/ml without extraction.

TABLE I

Recovery of lorazepam in biological fluids with extraction with ethyl acetate.

| Biological fluid | Lorazepam added ng/ml | found ng/ml | Recovery % |
|---|---|---|---|
| Saliva | 0 | 0.0 | |
| | 10 | 10.6 | 106 |
| Urine | 0 | 0.3 | |
| | 10 | 9.5 | 95 |
| Blood (citrate) | 0 | 0.0 | |
| | 10 | 10.4 | 104 |
| Blood (EDTA) | 0 | 0.0 | |
| | 10 | 9.3 | 93 |
| Blood (heparine) | 0 | 0.0 | |
| | 3 | 2.9 | 97 |
| | 10 | 9.0 | 90 |
| | 30 | 22.7 | 76 |
| Blood (heparine + NaF) | 0 | 0.0 | |
| | 3 | 2.5 | 83 |
| | 10 | 9.0 | 90 |
| | 30 | 25.4 | 85 |
| Serum | 0 | 0 | |
| | 10 | 9.1 | 91 |
| Plasma (citrate) | 0 | 0.0 | |
| | 10 | 10.4 | 104 |
| Plasma (EDTA) | 0 | 0.0 | |
| | 10 | 9.0 | 90 |
| Plasma (heparine) | 0 | 0.0 | |
| | 3 | 3.2 | 107 |
| | 10 | 9.2 | 90 |
| | 30 | 28.6 | 96 |

TABLE 2

Recovery of lorazepam in biological fluids. The determinations were carried out without extraction.

| Biological fluid | Lorazepam added ng/ml | found ng/ml | Recovery % |
|---|---|---|---|
| Saliva | 0 | 0 | |
| | 20 | 16 | 80 |
| Urine | 0 | 0 | |
| | 20 | 17.5 | 87 |
| Blood (heparine) | 0 | 9 | |
| | 100 | 115 | 115 |
| | 250 | 254 | 102 |
| | 500 | 486 | 97 |
| Plasma (heparine) | 0 | 10 | |
| | 100 | 99 | 99 |
| | 250 | 227 | 91 |
| | 500 | 409 | 82 |

We claim:

1. A process for determining the concentration of benzodiazepines in a body fluid, comprising the steps of contacting freeze-dried brain tissue with a radio-labelled benzodiazepine to form a preparation comprising said brain tissue and labelled benzodiazepine reversibly bonded thereto, determining the concentration of radio-labelled bound benzodiazepine in said preparation, contacting a sample of the body liquid or an extract of such liquid containing the benzodiazepine, the concentration of which is to be determined, with said preparation to establish an equilibrium between labelled and un-labelled benzodiazepine bonded to said brain tissue, determining the concentration of labelled benzodiazepine bonded to said brain tissue after establishing equilibrium conditions and calculating the concentration of benzodiazepine in the sample based on the change of concentration of labelled benzodiazepine in the brain tissue induced by benzodiazepines contained in the sample.

2. A process according to claim 1, comprising using a powdered freeze-dried brain tissue obtained from brain tissue of tetrapods and higher bony fish.

3. A process according to claim 1, comprising using a labelled benzodiazepine selected from a group consisting of tritium labelled 7-chloro-1,3-dihydro-1-methyl-5-phenyl-2H-1,4-benzodiazepin-2-one (diazepam) and 7-nitro-1,3-dihydro-1-methyl-5-(2-fluorophenyl)-2H-1,4-benzodiazepin-2-one (flunitrazepam).

4. A process according to claim 1, wherein the determination of the concentration of radio-labelled benzodiazepine in the preparation before it is contacted with the sample is effected by scintillation counting.

5. A process according to claim 1, comprising incubating the sample with the preparation at room temperature for a period of from 10 to 120 minutes.

6. A process according to claim 1, comprising determing the concentration of radio-labelled benzodiazepine in said preparation by scintillation counting after establishing equilibrium conditions.

7. A process according to claim 5, comprising filtering the incubated mixture of the sample and the preparation to isolate the brain tissue.

8. A reagent for use in the process according to claim 1, comprising freeze-dried animal brain tissue.

9. A reagent according to claim 8, comprising powdered freeze-dried brain tissue selected from a group consisting of ox, pig, sheep, rat and hen brain tissue.

10. A process of preparing a reagent according to claim 8, comprising homogenizing animal brain tissue to an aqueous solution of an inert water soluble substance and freeze-drying the homogenate thus obtained.

11. A process according to claim 10, wherein the inert water soluble substance is a sugar.

12. A process according to claim 11, wherein said sugar is sucrose.

13. A kit for use in carrying out the process according to claim 1 comprising (a) a container containing freeze-dried animal brain powder,
(b) a vial containing a solution of radio-labelled benzodiazepine,
(c) a container containing a buffer solution and
(d) a container containing a solution of a predetermined amount of unlabelled benzodiazepine.

* * * * *